United States Patent
Toda et al.

(10) Patent No.: US 9,358,360 B2
(45) Date of Patent: Jun. 7, 2016

(54) ILLUMINATION APPARATUS

(71) Applicant: PANASONIC INTELLECTUAL PROPERTY MANAGEMENT CO., LTD., Osaka (JP)

(72) Inventors: Naohiro Toda, Osaka (JP); Kazuhiro Hatta, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 14/848,473

(22) Filed: Sep. 9, 2015

(65) Prior Publication Data

US 2016/0074620 A1 Mar. 17, 2016

(30) Foreign Application Priority Data

Sep. 12, 2014 (JP) .................................. 2014-186262

(51) Int. Cl.
*A61M 21/00* (2006.01)
*H05B 33/08* (2006.01)
*H05B 37/02* (2006.01)

(52) U.S. Cl.
CPC ........... *A61M 21/00* (2013.01); *H05B 33/0845* (2013.01); *H05B 33/0863* (2013.01); *H05B 37/0281* (2013.01); *A61M 2021/0011* (2013.01); *A61M 2021/0083* (2013.01)

(58) Field of Classification Search
CPC ........... H05B 33/0845; H05B 33/0815; H05B 33/0818; H05B 33/0809; H05B 33/0851; H05B 33/0827; H05B 33/086; H05B 37/02; H05B 33/0866; Y02B 20/46; G09G 2320/064; G09G 2320/0646; G09G 2360/16; G09G 3/3406; G09G 3/3426; G09G 3/364
See application file for complete search history.

(56) References Cited

U.S. PATENT DOCUMENTS

| | | | | |
|---|---|---|---|---|
| 2012/0032616 | A1* | 2/2012 | Toda .................... | A61M 21/00 315/360 |
| 2013/0038244 | A1* | 2/2013 | Kamii .................. | H05B 33/086 315/297 |
| 2015/0305126 | A1* | 10/2015 | Maeda ............... | H05B 37/0227 315/134 |
| 2016/0081163 | A1* | 3/2016 | Hatta ................. | H05B 37/0227 315/312 |

FOREIGN PATENT DOCUMENTS

| | | |
|---|---|---|
| JP | H04-264289 | 9/1992 |
| JP | H07-318670 | 12/1995 |

* cited by examiner

*Primary Examiner* — Jany Richardson
(74) *Attorney, Agent, or Firm* — Greenblum & Bernstein, P.L.C.

(57) ABSTRACT

In an illumination apparatus, a control unit starts lighting of a light source at a first time before a wake-up set time and executes a first control pattern to increase a dimming ratio of the light source from the first time to a second time determined based on the wake-up set time and a second control pattern to further increase the dimming ratio of the light source from the second time to a third time determined based on the wake-up set time. When a change curve of the dimming ratio in the first control pattern and the second control pattern is applied to a function represented by the equation: $Y(t)=d+(a-d)/(1+(t/c)^b)$, the time c becomes closer to the second time than the first time in the first control pattern, and becomes closer to the second time than the third time in the second control pattern.

10 Claims, 6 Drawing Sheets

SIGMOID CURVE
$Y(t) = d + (a - d) / (1 + (t/c)^b)$

ILLUMINATION APPARATUS

CROSS-REFERENCE TO RELATED APPLICATIONS

This application claims priority to Japanese Patent Application No. 2014-186262 filed on Sep. 12, 2014, the entire contents of which are incorporated herein by reference.

TECHNICAL FIELD

The present disclosure relates to an illumination apparatus for implementing an illumination environment suitable for awakening.

BACKGROUND ART

Conventionally, there is known an alarm illumination device which gradually increases the brightness of a light source from a predetermined time before a preset wake-up time such that a sleeping person can be comfortably awakened at the wake-up time (see, e.g., Japanese Patent Application Publication No. H4-264289). Also, there is known an illumination device which gently changes illuminance from low illuminance to medium illuminance, and rapidly changes illuminance from medium illuminance to high illuminance by using light of at least three types of illuminance, i.e., low illuminance, medium illuminance and high illuminance (see, e.g., Japanese Patent Application Publication No. H7-318670). According to the illumination device, it is possible to cause the biological rhythm of the sleeping person to enter into an active phase while guiding the sleep state of the sleeping person from a deep state to a shallow state.

However, in general, since many people get up after the consciousness is gradually awakened, it takes some time until they actually get up from waking up although there are individual differences. Accordingly, for example, as in the above-mentioned illumination device, when rapidly changing illuminance from medium illuminance to high illuminance, a person who has not been sufficiently awakened during the illuminance change from low illuminance to medium illuminance may feel uncomfortable because of the rapid illuminance change thereafter.

SUMMARY OF THE INVENTION

In view of the above, the present disclosure provides an illumination apparatus for allowing a sleeping person to comfortably wake up by illumination light and to effectively obtain wakefulness until he/she gets up.

In accordance with an aspect of the disclosure, there is provided an illumination apparatus including: a light source with a variable dimming ratio; and a control unit configured to control lighting of the light source.

The control unit is configured to start the lighting of the light source at a first time before a wake-up set time, and to execute a first control pattern to increase a dimming ratio of the light source from the first time to a second time determined based on the wake-up set time and a second control pattern to further increase the dimming ratio of the light source from the second time to a third time determined based on the wake-up set time.

The control unit is configured to change a dimming ratio of the first control pattern and the second control pattern in accordance with a function of time represented by the following equation:

$$Y(t) = d + (a-d)/(1+(t/c)^b)$$

(Y(t): dimming ratio, t: time, a: maximum dimming ratio, b: maximum slope, c: value corresponding to a moment at which change in dimming ratio over time becomes the maximum slope b, d: minimum dimming ratio).

In the first control pattern, the time t means a time elapsed between the first time and the second time, the value c is a time elapsed since the first time and the moment corresponding to the value c is closer to the second time than the first time.

In the second control pattern, the time t means a time elapsed between the second time and the third time, the value c is a time elapsed since the second time and the moment corresponding to the value c is closer to the second time than the third time.

With such configurations, in a first control mode, by switching the changing pattern of the dimming ratio from a gradually changing pattern to a sharply changing pattern, a sleeping person can comfortably wake up. Further, in a second control mode, by switching the changing pattern of the dimming ratio from the sharply changing pattern to the gradually changing pattern, the person can effectively obtain wakefulness until he/she gets up.

BRIEF DESCRIPTION OF THE DRAWINGS

The figures depict one or more implementations in accordance with the present teaching, by way of example only, not by way of limitations. In the figures, like reference numerals refer to the same or similar elements.

FIGS. 2A to 2C show the illumination apparatus, in which

DETAILED DESCRIPTION

Figure 1:
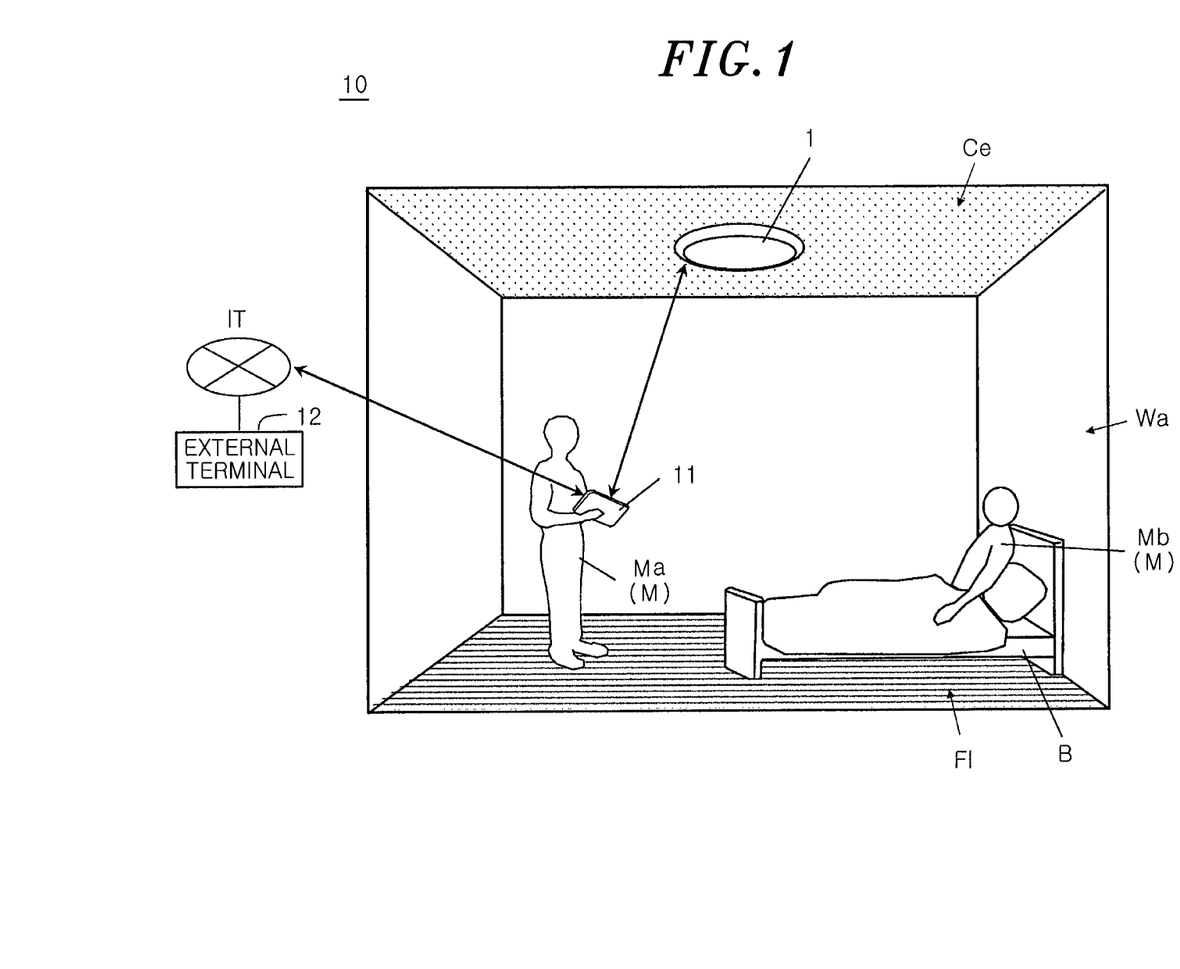
FIG. 1 is a diagram showing an indoor space to which an illumination system using an illumination apparatus according to an embodiment of the present invention is applied.

Hereinafter, an illumination apparatus according to an embodiment of the present invention will be described with reference to FIGS. 1 to 7. As shown in FIG. 1, an illumination apparatus 1 according to an embodiment of the present disclosure is used in an illumination system 10, and suitably used in a bedroom where a bed B is placed to irradiate light to an indoor space including a wall surface Wa and a floor surface Fl. The present embodiment will be described in conjunction with a configuration example where the illumination apparatus 1 is applied as a ceiling light attached to a ceiling surface Ce (installation surface). However, the illumination apparatus 1 is not limited to a ceiling light, and may be, e.g., a downlight, a bracket, or a desk stand, as long as they can illuminate the periphery of a sleeping person.

The turn-on operation of the illumination apparatus 1 can be controlled by a user M (Ma or Mb) who manipulates a terminal 11. The terminal 11 functions as an input terminal for inputting a wake-up set time to be described later. The user M may register and set various control patterns of the illumination apparatus 1 by operating the terminal 11. The terminal 11 may be a remote controller dedicated to the illumination apparatus 1 or may be an information communication terminal such as a smartphone or a tablet terminal. If the terminal 11 is an information communication terminal, the terminal 11 is preferably connected to an external terminal 12 such as an external server through the Internet IT.

Figure 2A:
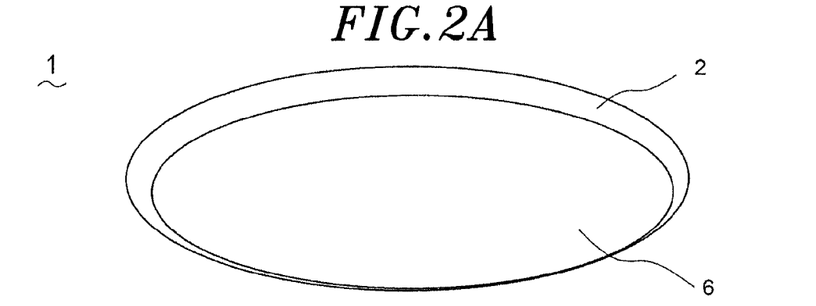
FIG. 2A is a perspective view of the illumination apparatus.
Figure 2B:
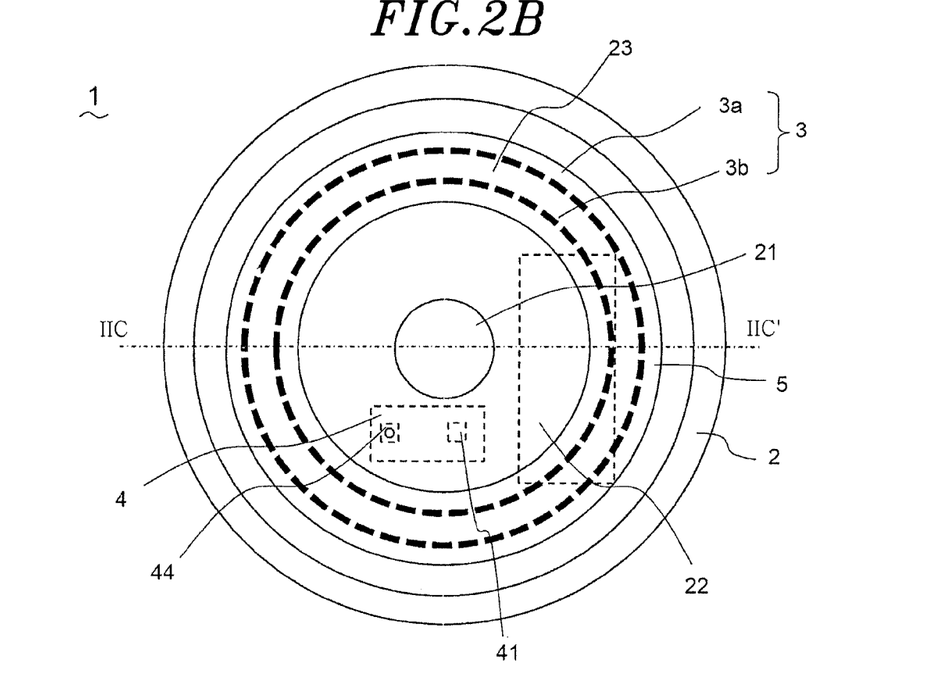
FIG. 2B is a bottom view of the illumination apparatus from which a cover is removed.
Figure 2C:
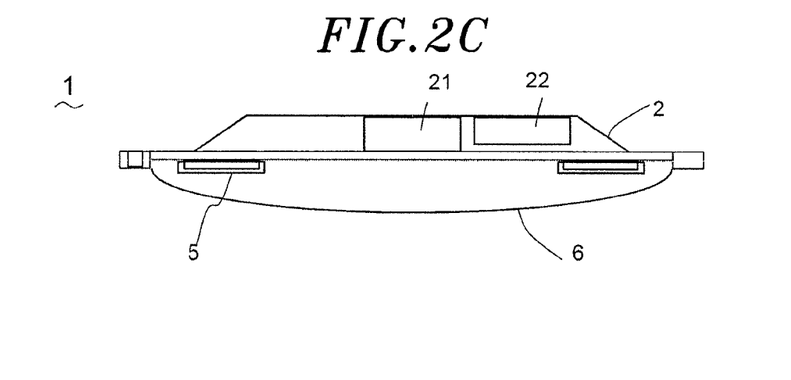
FIG. 2C is a cross-sectional view taken along line IIC-IIC' of FIG. 2B.

As shown in FIGS. 2A to 2C, the illumination apparatus 1 includes a body 2, a light source (LEDs) 3 disposed in a ring shape about the center of the body 2, and an optical member 5 provided at the light emission side of the light source 3 and configured to control distribution of the light emitted from the light source 3. The illumination apparatus 1 further includes a diffusion member (cover) 6 provided at the light emission side of the optical member 5 and configured to diffuse and radiate the light emitted from the optical member 5.

The light source 3 is formed of two concentric lines of LED groups 3a and 3b, each of which includes a plurality of LEDs disposed in a ring shape. The outer peripheral LED group 3a is composed of LED chips which irradiate light having a relatively-high color temperature. The inner peripheral LED groups 3b is composed of LED chips which irradiate light having a relatively-low color temperature. In the present embodiment, a configuration in which two lines of LED groups are disposed is illustrated as the light source 3. However, the present invention is not limited thereto. Alternatively, it may be possible to use one line of LED group or three or more lines of LED groups. Each of the LED groups may be a fluorescent-lamp-type LED illumination device including LEDs accommodated therein.

The LEDs of the light source 3 are covered with a wavelength converting material which converts the wavelength of the light emitted from LED chips and are formed into LED packages. For example, GaN-based blue LED chips which emit blue light are used as the LED chips. A mixture of a seal-purpose light-transmitting resin material and a phosphor for the emission of light having a neutral white color or a light bulb color is used as the wavelength converting material. The color temperature of the light irradiated from the light source 3 may range from a daylight color to a light bulb color (from 7,100K to 2,600K). LED chips which emit light of a daylight color having a color temperature of, e.g., about 6,500K, are suitably used as the LED group 3a which irradiates light having a relatively-high color temperature. LED chips which emit light of a light bulb color having a color temperature of, e.g., about 2,700K, are suitably used as the LED group 3b which irradiates light having a relatively-low color temperature. By controlling the dimming ratio of the LED groups 3a and 3b, the light source 3 can appropriately change the color temperature of the irradiated light.

The body 2 is a plate-like member having a circular top-view shape, which is attached to the ceiling surface Ce with the upper surface (attachment surface) thereof facing the ceiling surface Ce. Examples of the body 2 include a die-cast member having a small thickness and a member formed of an iron plate, an aluminum pate or the like and one-piece molded into a specified shape. A mounting bracket (not shown) is provided in the central region of the upper surface of the body 2 and is connected to a ceiling hook or the like installed on the ceiling surface Ce. The light source 3 is disposed on the opposite surface of the body 2 from the ceiling surface Ce.

A power supply unit 21 fixed to a power supply connector provided on an installation surface is disposed in the central portion of the body 2. A lighting circuit 22 for turning on the light source 3 and a substrate 23 for mounting the LEDs of the light source 3 are provided at the outer peripheral side of the power supply unit 21. The body 2 is formed by pressing and cutting a plate such as an aluminum plate or a steel plate having a specified rigidity into the aforementioned shape. A white paint having high visible-light reflectivity may be coated, or a reflective metallic material may be vapor-deposited, on the surface of the body 2 on which the LEDs are disposed.

The power supply unit 21 is a general-purpose adaptor guide and is connected to a commercial AC power source via a power supply connector or the like. The lighting circuit 22 includes a voltage transformer, a capacitor and a control IC, which convert and rectify an AC current supplied from the power supply unit 21 into a DC current having a specified voltage suitable for the light source 3. The substrate 23 is made of an insulating material such as glass epoxy resin or the like. Specified wiring patterns are formed on the surface of the substrate 23 on which the light source 3 is mounted. The substrate 23 may be a resin-based substrate, a ceramic-made substrate or a substrate based on metal such as aluminum or the like. In addition, a flexible substrate or the like may be used as the substrate 23. The lighting circuit 22 is configured to independently turn on the outer peripheral LED group 3a and the inner peripheral LED group 3b in response to a user's manipulation. The LEDs of the respective LED groups 3a and 3b may be divided one by one or into a plurality of groups so that partial lighting or selective lighting can be performed.

A control unit 4 for controlling a turn-on operation of the light source 3 is provided in the substrate 23. Responsive to a wireless signal received from the terminal 11, the control unit 4 turns on or off the light source 3. The term "wireless" used herein includes infrared rays, electric waves and visible light. The control unit 4 performs dimming control of the light source 3 using, e.g., PWM (Pulse Width Modulation) control or analog dimming control. The control unit 4 includes a microcomputer 41. The term "dimming ratio" used herein means a ratio of brightness to the maximum brightness of the light source 3. For example, if the control unit 4 performs dimming control of the light source 3 using PWM control, the dimming ratio is decided by a duty ratio of a PWM signal.

The optical member 5 is a trough-shaped lens member which covers all the LEDs of the light source 3 disposed in a ring shape. The optical member 5 is made of a light-transmitting resin such as an acryl resin or the like. In the present embodiment, the optical member 5 is formed of semi-circular trough-shaped lens members which cover both the outer peripheral LED group 3a and the inner peripheral LED group 3b of the light source 3.

The cover 6 is formed into a dome shape so as to cover the front surface of the body 2 and is made of, e.g., a resin material obtained by adding light-diffusing particles or a pigment to a light-transmitting material such as an acryl resin or the like. Instead of adding the light-diffusing particles or the pigment, the cover 6 may be formed by subjecting the front surface or the rear surface of a glass substrate or a resin substrate to a sandblast process so as to become a rough surface, subjecting the front surface or the rear surface of a glass substrate or a resin substrate to a surface texturing process, or subjecting the front surface or the rear surface of a glass substrate or a resin substrate to a dimple forming process so as to form fine irregularities.

Figure 3:
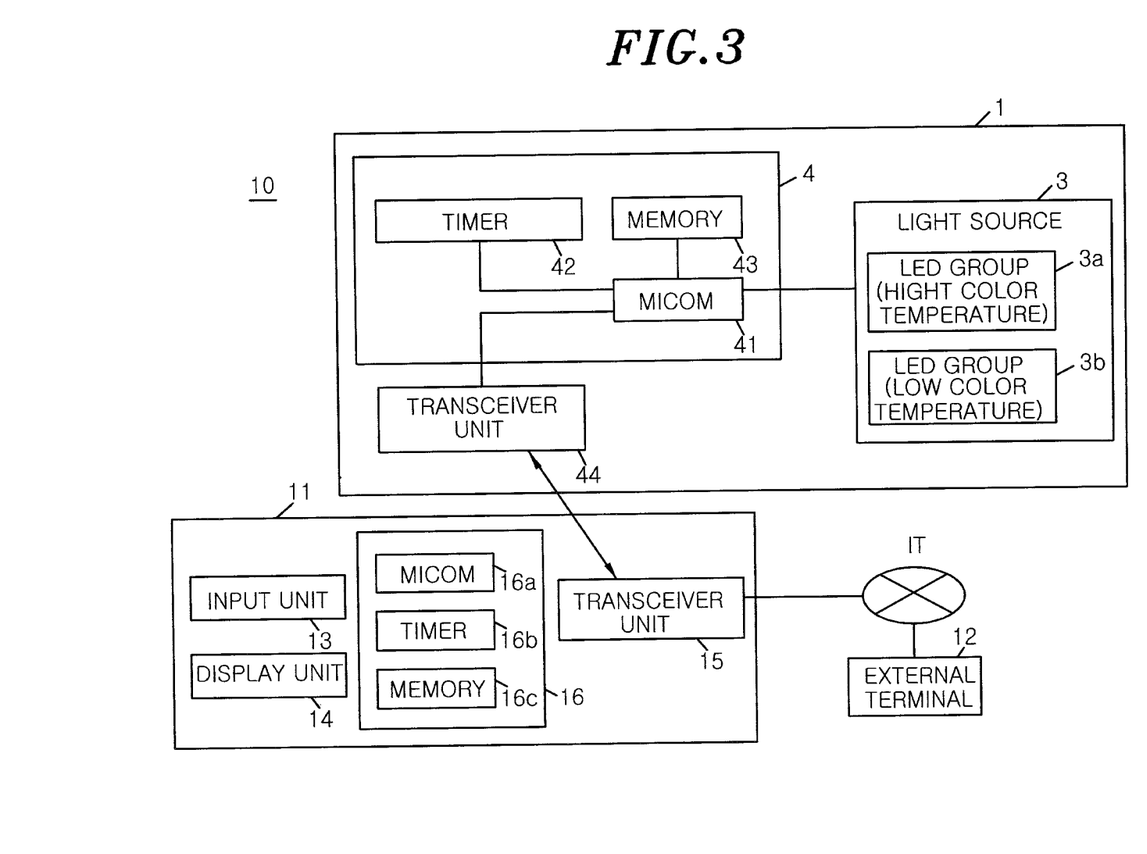
FIG. 3 is a block diagram of the illumination system using the illumination apparatus.

As shown in FIG. 3, the control unit 4 includes a timer 42 for counting a time and a memory 43 for storing data such as the dimming ratio of the light source 3 for the time counted by the timer 42 and the past illumination information. The illumination apparatus 1 further includes a transceiver unit 44 for transmitting and receiving a control signal or other signals to and from the terminal 11.

The terminal 11 includes an input unit 13 for setting a dimming mode of the illumination apparatus 1 at a bedtime and a wakeup time, a display unit 14 for displaying an input content, and a transceiver unit 15 (or a terminal transceiver unit) for making communications with the illumination apparatus 1. The input unit 13 is an input interface and is configured by, e.g., a push-button-type switch, a touch panel or the like. The transceiver unit 15 performs communication using, e.g., an infrared communication method, a communication method of ZigBee (registered trademark) which is one of standards of WPAN (Wireless Personal Area Network), or other communication methods. The terminal 11 further includes a control unit 16 which accommodates therein a microcomputer 16a for controlling the respective components mentioned above, a timer 16b and a memory 16c.

The control unit 4 of the illumination apparatus 1 starts the lighting of the light source 3 at a first time earlier than a wake-up set time which is previously set by the user with the terminal 11. The control unit 4 executes two control patterns, i.e., first and second control patterns to be described below, as lighting control patterns of the light source 3. The first control pattern increases the dimming ratio of the light source 3 from the first time to a second time determined based on the wake-up set time. The second control pattern further increases the dimming ratio of the light source 3 from the second time to a third time determined based on the wake-up set time.

Here, a change curve of the dimming ratio in the first control pattern and the second control pattern may be applied to a function (regression curve) represented by the following Eq. 1.

$$Y(t) = d + (a-d)/(1+(t/c)^b)$$ Eq.1

(Y(t): dimming ratio, t: time, a: maximum dimming ratio, b: maximum slope, c: value (time) corresponding to a moment at which change in dimming ratio over time becomes the maximum slope b, d: minimum dimming ratio)

Figure 4:
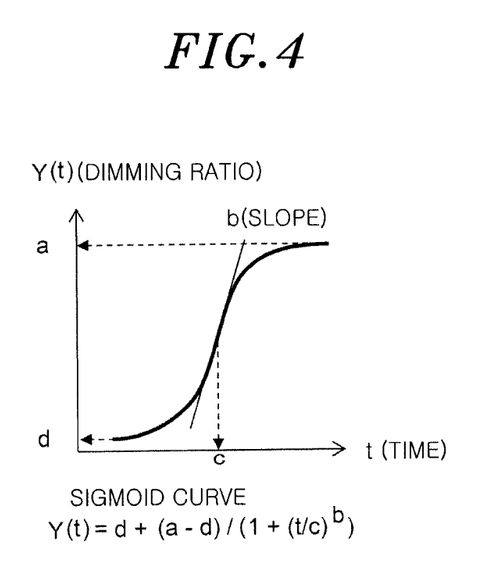
FIG. 4 shows illumination information of the indoor space to which the illumination system using the illumination apparatus is applied.

The regression curve is called a sigmoid curve as shown in FIG. 4. When the dimming ratio Y(t) is plotted on the y-axis and the time t is plotted on the x-axis, the change curve of the dimming ratio of this example has approximately asymptotic lines at the maximum dimming ratio a and the minimum dimming ratio d. A curve which is convex in a downward direction is drawn at a time earlier than the time c corresponding to the maximum slope b, and a curve which is convex in an upward direction is drawn at a time later than the time c. Further, in the time t of the above regression curve, the lighting start time of the light source 3 is set as 0 second. However, a change curve of the dimming ratio to be described later shows the dimming ratio with respect to the time, and the time that is a predetermined time (e.g., 2100 seconds (35 minutes)) earlier than the wake-up set time which is previously set by the user corresponds to the 0 second.

Figure 5:
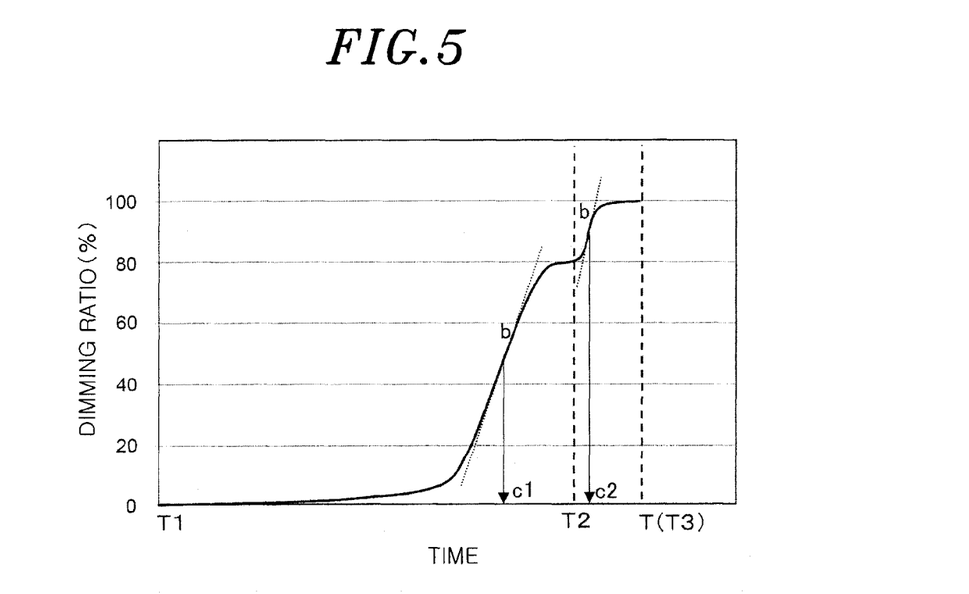
FIG. 5 is a time chart showing a change example of the dimming ratio in the illumination apparatus.

FIG. 5 shows the change curve of the dimming ratio of the illumination apparatus 1 in accordance with the present embodiment. First, the user M sets an arbitrary wake-up set time T by using the terminal 11. At the time earlier than the wake-up set time T, the control unit 4 of the illumination apparatus 1 sets a first time T1 to start the lighting of the light source 3, a second time T2 to provide an illumination environment suitable for awakening the user M, and a third time T3 to provide an illumination environment suitable for arousing the user M. The operation of the control unit 4 may be executed by the control unit 16 of the terminal 11.

In the present embodiment, e.g., the first time T1 is 35 minutes before the wake-up set time T, and the second time T2 is 5 minutes before the wake-up set time T. The first time T1 and the second time T2 may be set automatically by the user M inputting the wake-up set time T, or either or both of the first time T1 and the second time T2 may be settable by the user. In this example, the third time T3 is the same time as the wake-up set time T. However, the third time T3 may be a time different from the wake-up set time T, and may be set by the user M.

In accordance with the present embodiment, in the first control pattern executed from the first time T1 to the second time T2, the time c in the regression curve becomes closer to the second time T2 than the first time T1. That is, since the time c is a value corresponding to the maximum slope b in the change curve of the dimming ratio of the first control pattern, the time c indicates a time (shown as a time c1 in FIG. 5) at which an increasing rate of the dimming ratio is the highest in the first control pattern, and the time c1 is closer to the second time T2 than the first time T1.

That is, in the first control pattern, the change curve of the dimming ratio from the first time T1 to the second time T2 is convex downward. Thus, by maintaining a low dimming ratio immediately after the lighting start and gradually increasing the dimming ratio to increase the amount of light reaching the user M, the sleep state of the user M is changed to a shallow state. Subsequently, after the time c1 close to the second time T2, by giving a light stimulus to the user M by sharply increasing the dimming ratio, the illumination apparatus 1 may allow the user M to feel a smooth awakening at the second time T2.

Then, in the second control pattern executed from the second time T2 to the third time T3, the time c in the regression curve becomes closer to the second time T2 than the third time T3. That is, since the time c is a value corresponding to the maximum slope b in the change curve of the dimming ratio of the second control pattern, the time c indicates a time (shown as a time c2 in FIG. 5) at which an increasing rate of the dimming ratio is the highest in the second control pattern, and the time c2 is closer to the second time T2 than the third time T3.

That is, in the second control pattern, the change curve of the dimming ratio from the second time T2 to the third time T3 is convex upward. Therefore, by sharply increasing the dimming ratio in a short period after the second time T2 to further increase the amount of light reaching the user M, the illumination apparatus 1 arouses user's consciousness by increasing the amount of light received after awakening of the user M. Subsequently, after the time c2 close to the second time T2, by gradually increasing the dimming ratio, it is possible to cause the user M to smoothly reach wakefulness enough to get up.

According to the illumination apparatus 1 configured as described above, in a first control mode, by switching the changing pattern of the dimming ratio from a gradually changing pattern to a sharply changing pattern, a sleeping person can be comfortably awakened. Further, in a second control mode, by switching the changing pattern of the dimming ratio from the sharply changing pattern to the gradually changing pattern, the user M can effectively obtain wakefulness until he/she gets up.

Figure 6:
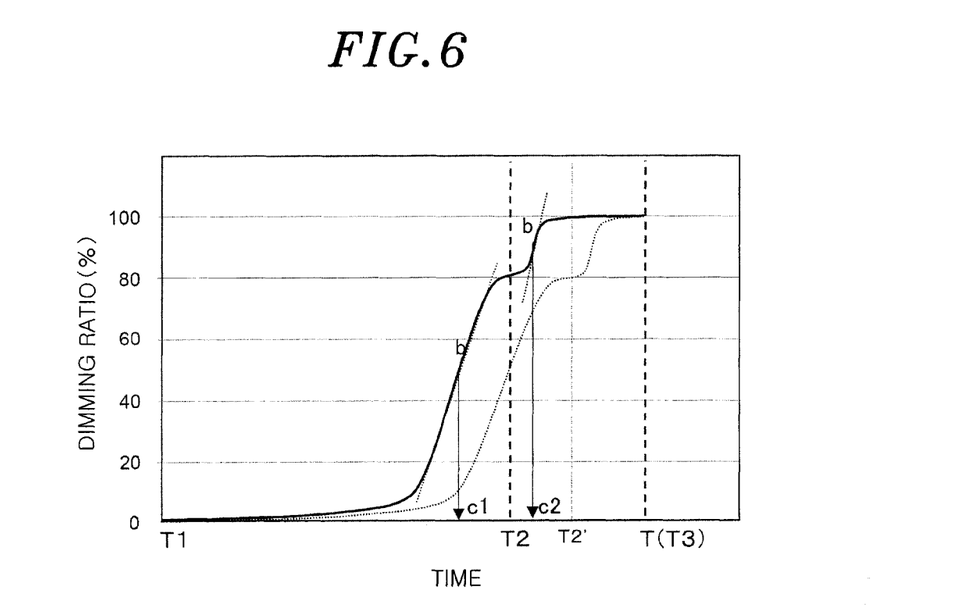
FIG. 6 is a time chart showing another change example of the dimming ratio in the illumination apparatus.

Also, e.g., as shown in FIG. 6, by allowing the user to arbitrarily set the second time T2, the user M can appropriately adjust the time of awakening or getting up according to his/her wakeup pattern. Further, by setting both of the second time T2 and the third time T3, it is possible to more finely set the time of awakening and the time of getting up. FIG. 6 also illustrates the second time shown in FIG. 5 as T2' and the change curve of the dimming ratio at that time.

Figure 7:
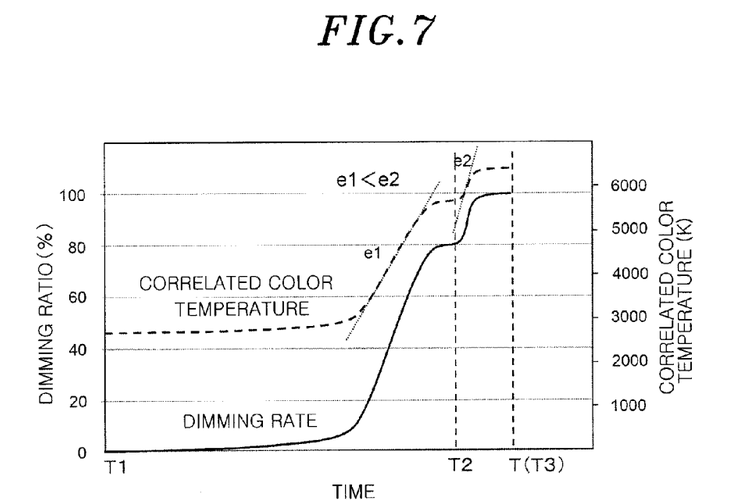
FIG. 7 is a time chart showing a change example of the dimming ratio and the correlated color temperature in the illumination apparatus.

In the illumination apparatus 1, as described above, the light source 3 is configured such that the correlated color temperature is variable. Therefore, as shown in FIG. 7, the control unit 4 increases the correlated color temperature of the light source 3 from the first time T1 to the third time T3. It is preferable that the increasing pattern (dashed-line curve in FIG. 7) of the correlated color temperature is controlled to follow a sigmoid curve, similarly to the change pattern (solid-line curve in FIG. 7) of the dimming ratio.

For example, when the correlated color temperature of the illumination light is high while the indoor space is dark, it gives a dismal impression. On the other hand, when the correlated color temperature of the illumination light is low while the indoor space is bright, it may give a stifling impression. In the above embodiment, e.g., when controlling only the dimming ratio, if the consciousness of the user M is somewhat awakened, a relationship between the indoor brightness and the correlated color temperature may cause discomfort to the user M. Therefore, as described above, by increasing the correlated color temperature as well as the dimming ratio, it is possible to suppress the discomfort to the user M as described above.

Preferably, in a period from the second time T2 to the third time T3, an increase of the correlated color temperature per time is large as compared to a period from the first time T1 to the second time T2. That is, in the change curve of the correlated color temperature, as shown in FIG. 7, a slope e2 between the second time T2 and the third time T3 is larger than a slope e1 between the first time T1 and the second time T2. Generally, by using light of a high color temperature, which is known to have a high effect of arousing human consciousness, in the period from the second time T2 to the third time T3, the arousal effect in the same period can be further increased.

Figure 8:
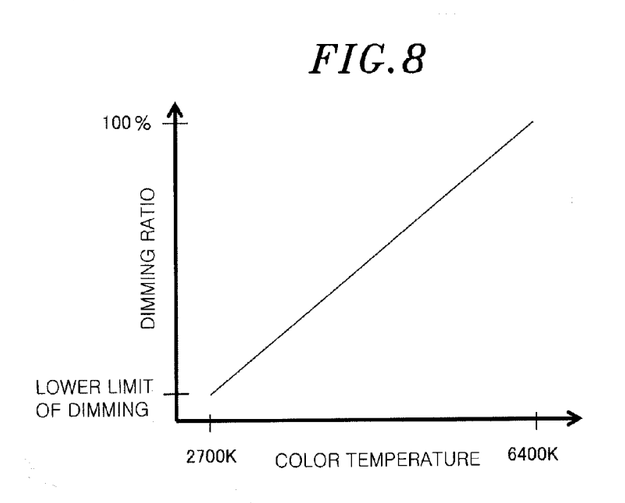
FIG. 8 is a diagram showing the correlation of the dimming ratio and the correlated color temperature in the illumination apparatus.

Further, preferably, a relationship between a change in the dimming ratio and a change in the correlated color temperature is substantially linear as shown in FIG. 8. In this case, it is possible to provide a natural illumination environment without giving the discomfort to the user M due to a relationship between changes in the indoor brightness and the correlated color temperature.

The present invention may be modified in various ways without being limited to the above-described embodiments. For example, if the transceiver unit 15 of the terminal 11 is connected to the external terminal 12 through the Internet IT, the illumination system 10 (see FIG. 1) can be connected to various networks and cloud systems, and for example, users can compare and refer to information. Also, for example, it is possible to introduce a service for giving an advice or setting a target value regarding illumination information such as setting the color temperature in the above-described sleeping control mode.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present teachings.

What is claimed is:

1. An illumination apparatus comprising:
a light source a dimming ratio of which is adjustable; and
a control unit configured to control the light source,
wherein the control unit is configured to start lighting of the light source at a first time before a wake-up set time, and to execute a first control pattern where the dimming ratio of the light source increases from the first time to a second time determined based on the wake-up set time and a second control pattern where the dimming ratio of the light source further increases from the second time to a third time determined based on the wake-up set time,
wherein the control unit is configured to change the dimming ratio in the first control pattern and the second control pattern in accordance with a function of time represented by a following equation:

$$Y(t)=d+(a-d)/(1+(t/c)^b)$$

where Y(t) is the dimming ratio; t is a time; a is a maximum dimming ratio; b is a maximum slope; c represents a value corresponding to a moment at which change in dimming ratio over time becomes the maximum slope b; and d is a minimum dimming ratio,
wherein in the first control pattern, the time t means a time elapsed between the first time and the second time, the value c is a time elapsed since the first time and the moment corresponding to the value c is closer to the second time than the first time, and
wherein in the second control pattern, the time t means a time elapsed between the second time and the third time, the value c is a time elapsed since the second time and the moment corresponding to the value c is closer to the second time than the third time.

2. The illumination apparatus of claim 1, further comprising an input unit configured to enable a user to set at least one of the second time and the third time.

3. The illumination apparatus of claim 1, wherein a correlated color temperature of the light source is adjustable, and
wherein the control unit increases the correlated color temperature of the light source from the first time to the third time.

4. The illumination apparatus of claim 2, wherein a correlated color temperature of the light source is adjustable, and
wherein the control unit increases the correlated color temperature of the light source from the first time to the third time.

5. The illumination apparatus of claim 3, wherein an increased amount of the correlated color temperature per time during a period from the second time to the third time is larger than an increased amount of the correlated color temperature per time during a period from the first time to the second time.

6. The illumination apparatus of claim 4, wherein an increased amount of the correlated color temperature per time during a period from the second time to the third time is larger than an increased amount of the correlated color temperature per time during a period from the first time to the second time.

7. The illumination apparatus of claim 3, wherein a relationship between a change in the dimming ratio and a change in the correlated color temperature is linear.

8. The illumination apparatus of claim 4, wherein a relationship between a change in the dimming ratio and a change in the correlated color temperature is linear.

9. The illumination apparatus of claim 5, wherein a relationship between a change in the dimming ratio and a change in the correlated color temperature is linear.

10. The illumination apparatus of claim 6, wherein a relationship between a change in the dimming ratio and a change in the correlated color temperature is linear.

* * * * *